(12) United States Patent
Smith et al.

(10) Patent No.: US 10,588,635 B2
(45) Date of Patent: Mar. 17, 2020

(54) WIDE HEMOSTASIS CLIP

(71) Applicant: BOSTON SCIENTIFIC SCIMED, INC., Maple Grove, MN (US)

(72) Inventors: Paul Smith, Smithfield, RI (US); Ray H. Tong, Foxborough, MA (US); Kevin McElwee, Franklin, MA (US); Shawn Ryan, Littleton, MA (US); Matthew R. Jagelski, Marlborough, MA (US); Norman May, Valrico, FL (US); Naroun Suon, Lawrence, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 302 days.

(21) Appl. No.: 15/597,967

(22) Filed: May 17, 2017

(65) Prior Publication Data

US 2017/0333040 A1  Nov. 23, 2017

Related U.S. Application Data

(60) Provisional application No. 62/338,213, filed on May 18, 2016.

(51) Int. Cl.
*A61B 17/10* (2006.01)
*A61B 17/122* (2006.01)
(Continued)

(52) U.S. Cl.
CPC ........ *A61B 17/10* (2013.01); *A61B 17/00234* (2013.01); *A61B 17/083* (2013.01);
(Continued)

(58) Field of Classification Search
CPC ... A61B 17/083; A61B 17/1227; A61B 17/10; A61B 17/00234; A61B 2017/00238;
(Continued)

(56) References Cited

U.S. PATENT DOCUMENTS 8,080,021 B2 * 12/2011 Griego ................ A61B 17/068
606/143
2002/0045909 A1  4/2002 Kimura et al.
(Continued)

FOREIGN PATENT DOCUMENTS

WO   2011/041571   4/2011
WO   2012/151415   11/2012
(Continued)

*Primary Examiner* — Gregory A Anderson
(74) *Attorney, Agent, or Firm* — Fay Kaplun & Marcin, LLP

(57) ABSTRACT

A device for treating tissue includes a capsule extending longitudinally from a proximal end to a distal end and including a channel extending therethrough, the capsule releasably coupled to a proximal portion of the device and clip jaws, proximal ends of which are slidably received within the channel of the capsule so that the clip jaws are movable between an open configuration and a closed configuration. Clip jaws are configured so that a distance between the distal ends of the clip jaws in an open configuration is between 15 and 18 millimeters. Clip jaws further include barbs extending from a distal portion thereof.

15 Claims, 6 Drawing Sheets

(51) Int. Cl.
*A61B 17/00* (2006.01)
*A61B 17/08* (2006.01)

(52) U.S. Cl.
CPC .............................. *A61B 17/1227* (2013.01); *A61B 2017/00238* (2013.01); *A61B 2017/00526* (2013.01); *A61B 2017/00818* (2013.01); *A61B 2017/00862* (2013.01)

(58) Field of Classification Search
CPC ........... A61B 2017/00526; A61B 2017/00818; A61B 2017/00862
See application file for complete search history.

(56) References Cited

U.S. PATENT DOCUMENTS

| | | |
|---|---|---|
| 2010/0137887 A1 | 6/2010 | Crockett et al. |
| 2012/0209318 A1 | 8/2012 | Qadeer |
| 2014/0088616 A1 | 3/2014 | Clerc et al. |

FOREIGN PATENT DOCUMENTS

| | | |
|---|---|---|
| WO | 2014/170903 | 10/2014 |
| WO | 2015/179396 | 11/2015 |

\* cited by examiner

Mechanical Properties

Table 2
Typical Room Temperature Mechanical Properties

| Property | Condition | | | | | | | |
| --- | --- | --- | --- | --- | --- | --- | --- | --- |
| | A | T | TH 1050 | A 1750 | R 100 | RH 950 | C | CH 900 |
| UTS, ksi (MPa) | 130 (896) | 145 (1000) | 200 (1379) | 133 (917) | 175 (1207) | 235 (1620) | 220 (1517) | 265 (1827) |
| 0.2% YS, ksi (MPa) | 40 (276) | 100 (690) | 185 (1276) | 42 (290) | 115 (793) | 220 (1517) | 190 (1310) | 260 (1793) |
| Elongation, % in 2" (50.8 mm) | 35 | 9 | 9 | 19 | 9 | 6 | 5 | 2 |
| Hardness, Rockwell | B85 | C31 | C43 | B85 | C36.5 | C48 | C43 | C49 |

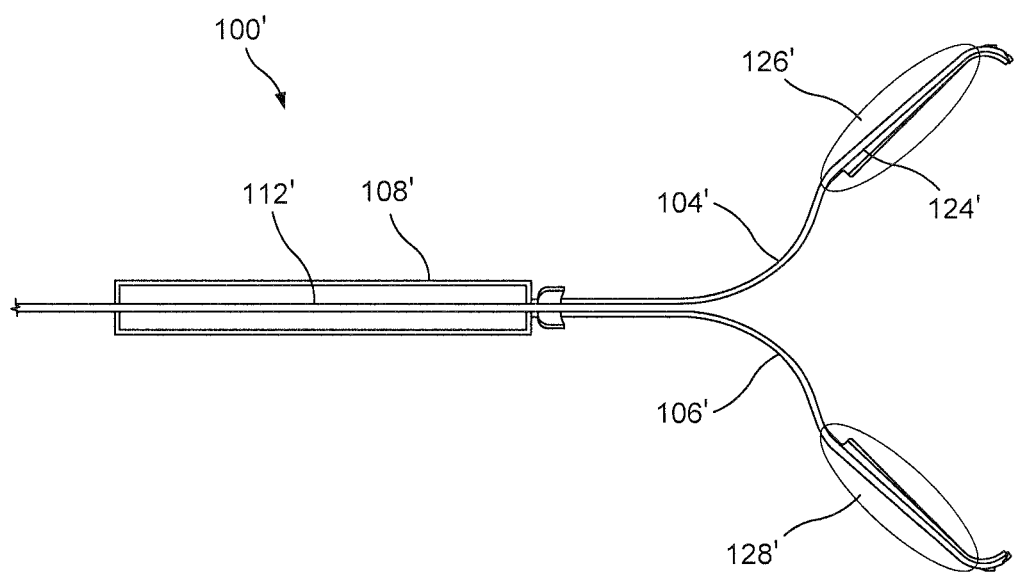
F I G. 5
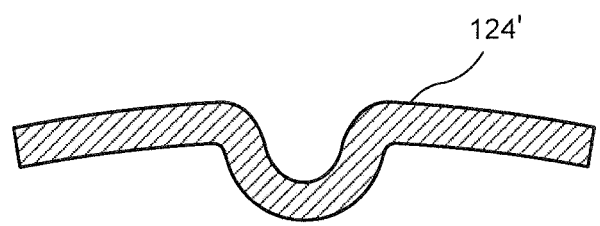
F I G. 6

WIDE HEMOSTASIS CLIP

PRIORITY CLAIM

The present disclosure claims priority to U.S. Provisional Patent Application Ser. No. 62/338,213 filed May 18, 2016; the disclosure of which is incorporated herewith by reference

BACKGROUND

Physicians have become more willing to perform more aggressive interventional and therapeutic endoscopic procedures including, for example, removal of larger lesions (e.g., cancerous masses), tunneling under mucosal layers in the gastro-intestinal (GI) tract to treat tissues below the mucosa, full thickness removal of tissue, inserting devices through the GI tract and then penetrating the GI organ to treat tissue outside the GI tract, and endoscopic treatment/repair of post-surgical issues (e.g., post-surgical leaks, breakdown of surgical staple lines, anastomotic leaks). These procedures may increase the risk of perforating or damaging the wall of the GI tract, or may require closure of the GI tract wall as part of the procedure. Endoscopic closure reduces cost and may reduce the trauma and inconvenience associated with these procedures. However, conventional tissue closure devices may be insufficient to close certain larger tissue defects. For example, current Resolution clips in the field may be deformed to have a jaw tip to jaw tip distance of approximately 10 to 12 millimeters before yielding. A wider jaw opening would allow more tissue to be clipped and treated for larger tissue issues.

SUMMARY

The present disclosure relates to a device for treating tissue, comprising a capsule extending longitudinally from a proximal end to a distal end and including a channel extending therethrough and clip jaws, proximal ends of which are slidably received within the channel of the capsule. The clip jaws are movable between an open configuration, in which distal ends of the clip jaws extend distally past the distal end of the capsule to be separated from one another, and a closed configuration, in which the clip jaws are restrained via an interior surface of the capsule so that distal ends of the clip jaws are drawn toward one another. A distance between the distal ends of the clip jaws in the open configuration is between 15 and 20 millimeters and at least one barb is coupled to a distal portion of the clip jaws.

The present disclosure also relates to a clipping device, comprising a proximal portion and a distal portion releasably coupled to the proximal portion so that the distal portion is deployable therefrom, the distal portion including a capsule extending longitudinally from a proximal end to a distal end and a including a channel extending therethrough, clip jaws extending from proximal ends slidably received within the channel of the capsule so that the clip jaws are movable between an open configuration, in which distal ends thereof extend distally past the distal end of the capsule to be separated from one another, and a closed configuration, in which the clip jaws are restrained via an interior surface of the capsule so that the distal ends thereof are drawn toward one another, a distance between distal ends of the clip jaws in the open configuration being between 15 and 20 millimeters and at least one barb coupled to a distal portion of the clip jaws, and a control member extending from a proximal end to a distal end, the distal end coupled to proximal ends of the clip jaws.

The present disclosure also relates to a method for treating target tissue, comprising inserting a distal portion of a clipping device to a target area within a living body, the distal portion including a capsule and clip jaws slidably received within the capsule to be movable between an open configuration, in which distal ends of the clip jaws are separated from one another, and a closed configuration, in which distal ends of the clip jaws are drawn toward one another, the clip jaws including a distance between distal ends of the clip jaws in the open configuration between 15 and 20 millimeters and at least one barb coupled to a distal portion of the clip jaws, positioning the clip jaws in contact with a target tissue, and clipping a target portion of tissue by positioning the target portion of tissue between the clip jaws in the open configuration and drawing the clip jaw toward the closed configuration to grip the target portion of tissue.

BRIEF DESCRIPTION

FIG. 5 shows a partially transparent longitudinal view of a device according to another alternate embodiment of the present disclosure;

FIG. 6 shows a cross-sectional view of the clip jaws of the device of FIG. 5;

DETAILED DESCRIPTION

Figures 1, 2:
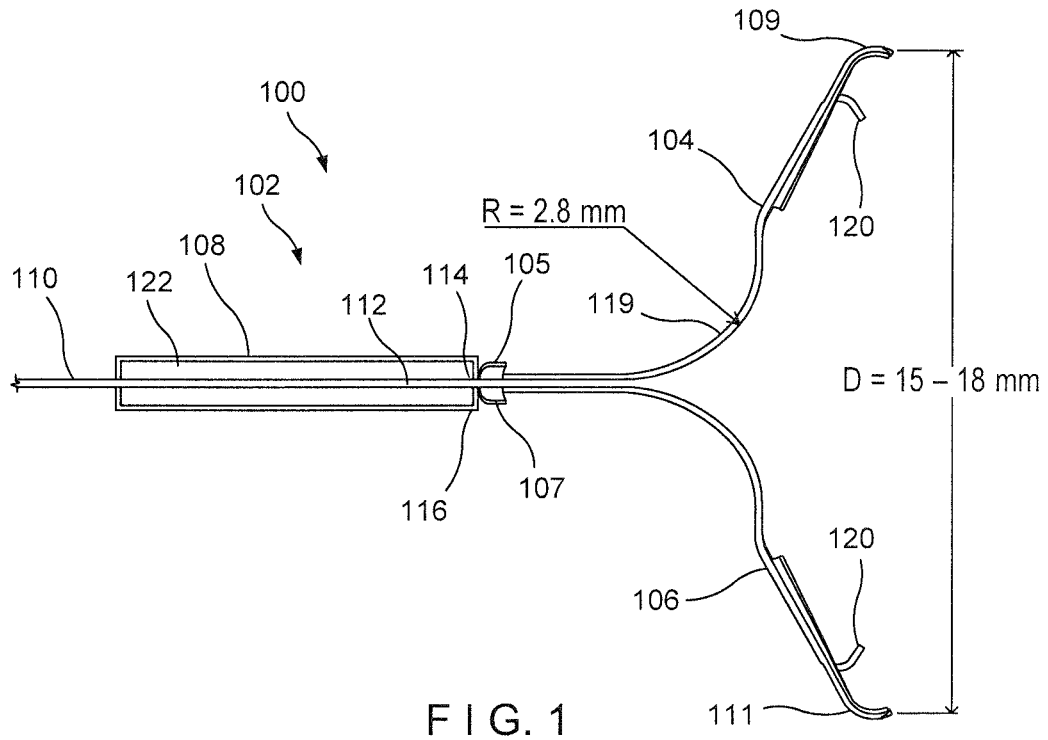
FIG. 1 shows a longitudinal cross-sectional view of a device according to an exemplary embodiment of the present disclosure.
FIG. 2 shows a table of mechanical properties for 17-7 Stainless Steel.

The present disclosure may be further understood with reference to the following description and the appended drawings, wherein like elements are referred to with the same reference numerals. The present disclosure is directed to an endoscopic clipping device for treating tissue perforations, defects and/or bleeds. Exemplary embodiments of the present disclosure describe a hemostatic clip having an increased jaw opening and features that allow better traction onto tissue to prevent tissue from sliding off jaws while closing. In particular, exemplary embodiments describe a hemostatic clip with clip jaws formed from a material treated to achieve an increased jaw tip to jaw tip distance to permit the clip to grab an increased volume of tissue. Portions of the clip jaws may include barbs or teeth to hold tissue when the clip is closed. It should be noted that the terms "proximal" and "distal," as used herein, are intended to refer to toward (proximal) and away from (distal) a user of the device.

As shown in FIG. 1, a device 100 according to an exemplary embodiment of the present disclosure comprises a distal portion 102 insertable into a living body through, for example, a working channel of an endoscope to target tissue to be treated. The device is sufficiently flexible to permit it to traverse a tortuous path through the body—e.g., passing through the working channel of an endoscope inserted through a natural body lumen accessed via a natural bodily orifice. The distal portion 102 includes first and second clip jaws 104, 106 slidably received within a longitudinal channel 122 of a capsule 108. First and second clip jaws 104,106 can be moved between an open configuration, in which the distal ends 109, 111 of the clip jaws 104,106 are separated from one another to receive target tissue therebetween, and a closed configuration, in which the distal ends 109, 111 of the clip jaws 104, 106 are moved toward one another to grip the target tissue therebetween. The distal portion 102 is releasably coupled to a proximal portion 110 of the device 100, which includes a handle (not shown) that remains outside the body accessible to a user as the distal portion 102 is deployed. The clip jaws 104, 106 are movable between the open and the closed configurations via a control member 112 extending into the capsule 108. A proximal end (not shown) of the control member 112 is connected to an actuator on the handle. In this embodiment, a distal end 114 of the control member 112 is coupled to proximal ends 116 of the clip jaws 104, 106.

As further shown in FIG. 1, device 100 includes clip jaws 104, 106 according to an exemplary embodiment of the present disclosure which extend from proximal ends 105, 107, respectively, to distal ends 109, 111, with a medial curved portion 119. As those skilled in the art will understand, jaws 104, 106 of this embodiment are biased toward an open tissue receiving position in which the distal ends 109, 111 are separated from one another to receive tissue. That is, the jaws 104, 106 are formed so that they spring open to the tissue receiving position when they are moved distally out of the constraint of the capsule 108. However, as would be understood by those skilled in the art, the device 100 may include a separate member urging the jaws 104, 106 away from one another in addition, or as an alternative, to this bias. In an exemplary embodiment, the clip jaws 104, 106 may have a jaw tip-to-jaw tip opening between 15 and 20 millimeters (mm) and, more particularly, between 16 and 18 millimeters. The clip jaws 104, 106 according to this embodiment may also have a length of between 2 and 3 mm greater than current clip jaws. Specifically, the clip jaws may be between 6 and 8 mm and, more particularly, a length of 7.5 mm. The clip jaws 104, 106 according to this embodiment are biased through the formation of the curved medial portion 119 which, is fabricated to include a resting radius of curvature (i.e., when unstressed) of approximately 3 mm or less and even more particularly has a radius of 2.8 mm or less. The radius of the medial curved portion is selected to maintain a desired spread distance between the distal ends 109 and 111 when the clip jaws 104, 106 are moved distally out of the capsule 108 by a maximum permitted extent. For example, in this embodiment, the desired spread distance is between 15-18 mm. As will be described in more detail below, the jaws 104, 106 are treated to achieve the desired spread distance without causing the material of the jaws 104, 106 to yield (i.e., plastically deform). In this embodiment, the clip jaws 104, 106 are formed of a material with a strain at yield above 0.7 percent with a yield strength greater than 200 kilopounds per square inch (ksi). This higher strain at yield and yield strength ensures that the clip jaws 104, 106 return to their original shape when drawn back into the capsule 108 and that they maintain their bias then return to the open configuration when extended again distally from the capsule 108. In an exemplary embodiment, the clip jaws 104, 106 are formed of 17-7 Stainless Steel, the mechanical properties of which are well known in the field of art. FIG. 2 provides the typical room temperature mechanical properties of 17-7 Stainless Steel after specific standard heat treatments. As would be understood by those skilled in the art, 17-7 Stainless Steel may be supplied at Condition A or Condition C, the properties of which are provided in FIG. 2. Condition RH-950 is accomplished by precipitation hardening from Condition C while Condition CH-900 is accomplished with a single low-temperature heat treatment from Condition C. In another embodiment, the 17-7 Stainless Steel clip jaws 104, 106 may be heat treated to an RH-950 or CH-900 condition as would be understood by those skilled in the art to increase a yield strength of the clip jaws 104, 106. Heat treating the clip jaws 104,106 may increase the strain at yield as high as 1.1 percent or a yield strength to as high as 260 ksi. Additionally materials such as Cobalt Chrome (Elgiloy) or Nitinol may also be used.

The clip jaws 104, 106 are biased toward the open configuration so that, when the clip jaws 104, 106 are moved distally past a distal end 116 of the capsule 108, distal ends 109, 111 of the clip jaws 104,106 separate from one another to the open configuration. When the clip jaws 104, 106 are drawn proximally into the capsule 108, contact with the capsule 108 draws the clip jaws 104, 106 toward one another to the closed configuration. They are then held in the closed position by the capsule 108. As described above, the clip jaws 104, 106 are moved between the open and closed configurations via the control member 112 which is moved proximally and distally relative to the capsule 108 via an actuator at a handle that remains outside the body.

Figure 3:
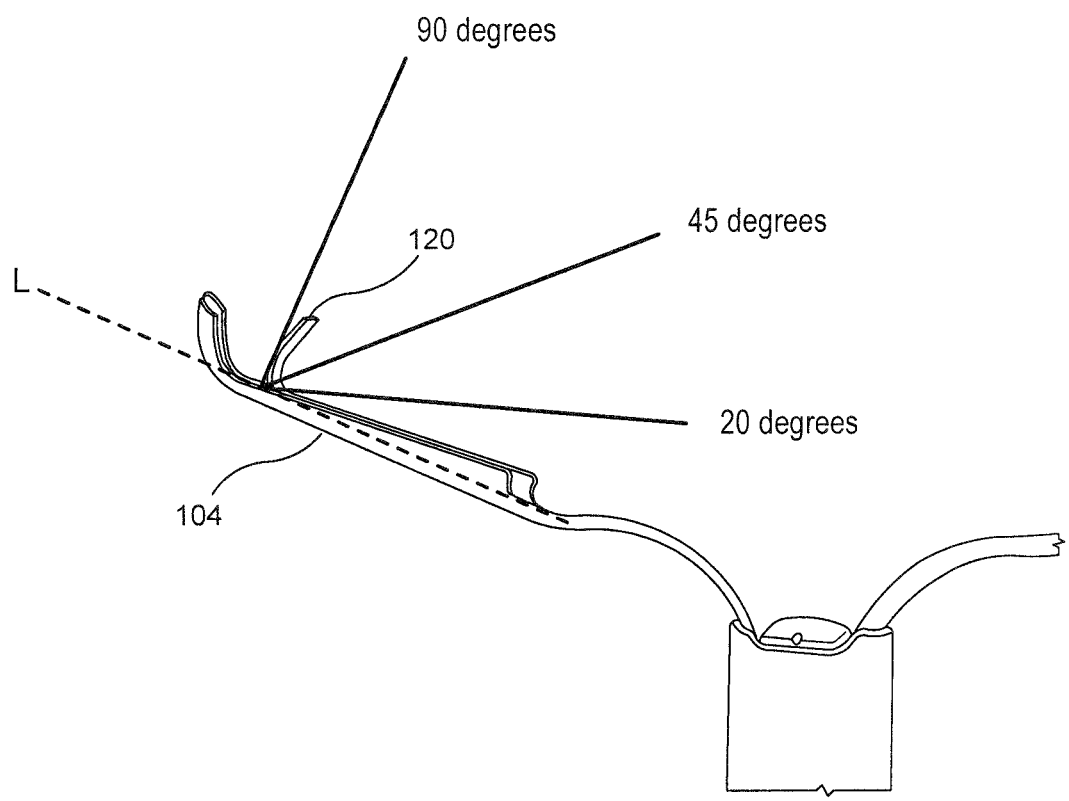
FIG. 3 shows a perspective view of the device of FIG. 1.
Figure 4:
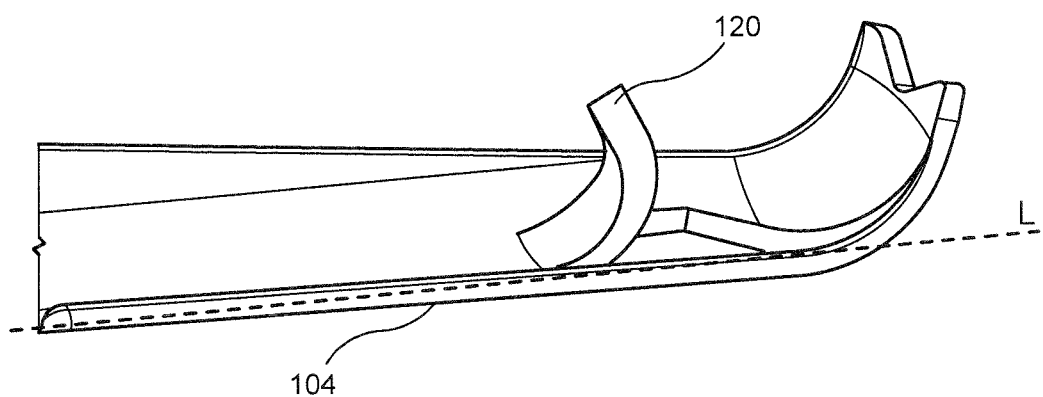
FIG. 4 shows a perspective view of a device according to another exemplary embodiment of the present disclosure.

Clip jaws 104, 106 include one or more hooks or barbs 120 attached to an interior side of a distal portion of clip jaws 104, 106. As shown in FIGS. 3-4, barbs 120 in this embodiment extend substantially perpendicularly from the interior face of jaws 104,106 radially inward toward the other of the jaws 104, 106. The barbs 120 may likewise extend from the interior face of jaws 104,106 at various angles between 20 and 90 degrees and, more particularly, 45 degrees relative to the longitudinal axis L of the jaw 104,106 to allow the barb 120 to grab tissue when the jaw 104,106 is in the open configuration. That is, the barb 120 may extend outward from the interior face of jaw 104,106 in a plane substantially perpendicular to a plane containing the interior face of each jaw 104,106 or may extend at an angle and thus in a plane that is not perpendicular to the plane containing the interior face of the jaw 104, 106. In an embodiment, the barb 120 is positioned so that when the clip is located adjacent to target tissue and the jaws 104, 106 are moved to the closed configuration, barbs 120 on each jaw 104, 106 are staggered or offset from one another longitudinally. In an alternative embodiment, the barbs 120 may be configured to extend in different planes so as to be received by an opposing jaw without interference from the barb 120 of the other jaw. In another embodiment, both of the barbs 120 may be configured to extend in substantially the same plane so that when jaws 104,106 are in a closed configuration ends of the barbs 120 from opposing jaws 104,106 touch one another. In an exemplary embodiment, as shown in FIG. 3, the barb 120 extends at an angle of 90 degrees relative to the flat jaw.

According to an exemplary method, the distal portion 102 of the device 100 may be inserted to a target area within a living body through, for example, a working channel of an endoscope. The distal portion 102 may be inserted through the working channel in the closed configuration. Once the distal portion 102 has reached the target area, however, the clip jaws 104, 106 may be moved to the open configuration by moving the control member 112 distally relative to the capsule 108. The clip jaws 104, 106 are movable between the open and closed configuration to grip and/or contact tissue in a manner which would achieve the desired effect. For example, for clipping, the distal ends 109, 111 of the clip jaws 104, 106 may be positioned about the area of the tissue to be clipped, in the open configuration. The clip jaws 104, 106 may be drawn toward the closed configuration so that the portion of the target area that is desired to be clipped is gripped between hooks or barbs 120 along the distal portion of the clip jaws 104, 106. The hooks or barbs 120 may be angled relative to the target tissue so that they do not drag along the target tissue but grab the tissue that is to be drawn into the capsule to be clipped. The clip jaws 104, 106 may be moved between the open and closed configurations until the desired portion of tissue is gripped. Once the portion of the tissue to be clipped has been positioned between the clip jaws 104, 106, the clip jaws 104, 106 are moved toward the closed configuration so that the tissue grabbed by the hooks or barbs 120 is gripped therebetween. The clip jaws 104, 106 are then moved further proximally into the capsule by the control member 112 so that the target tissue is firmly gripped between the clip jaws 104, 106 which are held in the closed configuration by the capsule. The capsule may then be separated from the proximal portion 110 of the device, deploying the clip in the body.

The above-described deployment process is one example of how the distal portion 102 of the device 100 may be deployed. The distal portion 102 may be deployed in a variety of different ways, depending on the configuration of the clip jaws 104, 106 and the capsule 108, so long as deployment releases the capsule 108 from a proximal portion 110 of the device while also locking the clip jaws 104, 106 in the closed configuration.

According to an alternate embodiment, as shown in FIGS. 5-6, a device 100' is substantially similar to the device 100 describe above, comprising distal portion 102' including clip jaws 104', 106' slidably received within a capsule 108' to be moved between an open configuration and a closed configuration via a control member 112'. Clip jaws 104', 106' may further include, in an exemplary embodiment, a rib feature 124' extending longitudinally across one or both of the jaws 104', 106'. As seen in the cross section of FIG. 6, the rib feature 124' extends along distal portions 126', 128' of the jaws 104', 106'. This rib feature 124' which may, for example, be stamped into the jaws 104', 106' increases a moment of inertia of the jaws 104', 106' in this region 126', 128' increases the resistance of the jaws 104',106' to bending or deforming even if the length of the jaws 104', 106' is increased. This extended length permits the device 100' to capture additional volume of tissue as compared to clips with shorter jaws. For example, the clip jaws 104', 106' may have as similar jaw tip-to-jaw tip opening as jaws 104, 106 of between 15 and 20 millimeters (mm) and, more particularly, between 16 and 18 millimeters.

The clip jaws 104', 106' according to this embodiment may also have a length of between 6 and 8 mm and, more particularly, a length of 7.5 mm, similar to clip jaws 104, 106. With this greater jaw tip-to-jaw tip opening, when the jaws 104', 106' are pushed into target tissue, the jaws 104', 106' tend to spread further to grasp even more tissue.

Figure 7:
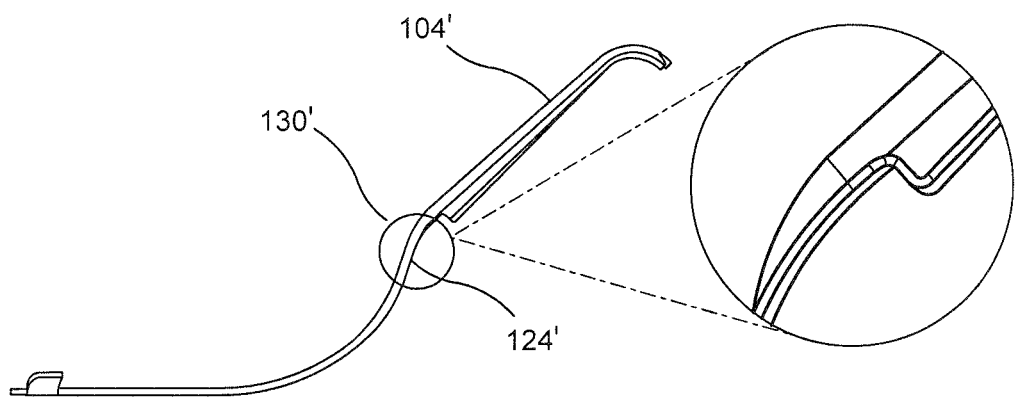
FIG. 7 shows a perspective top view of a device according to another exemplary embodiment of the present disclosure.

In another embodiment, shown in FIG. 7, the rib feature 124' may be stamped into the jaws 104', 106' at the C-Cup region 130' of the clip jaws 104', 106'. Including this stamp feature 124' at the C-Cup region 130' of the clip jaws 104', 106' increases a moment of inertia of the jaws 104', 106' in this region 130' so as to increase the resistance of the jaws and prevent the C-Cup region 130' from bending when pulled into the capsule while gripping captured tissue.

Figure 8:
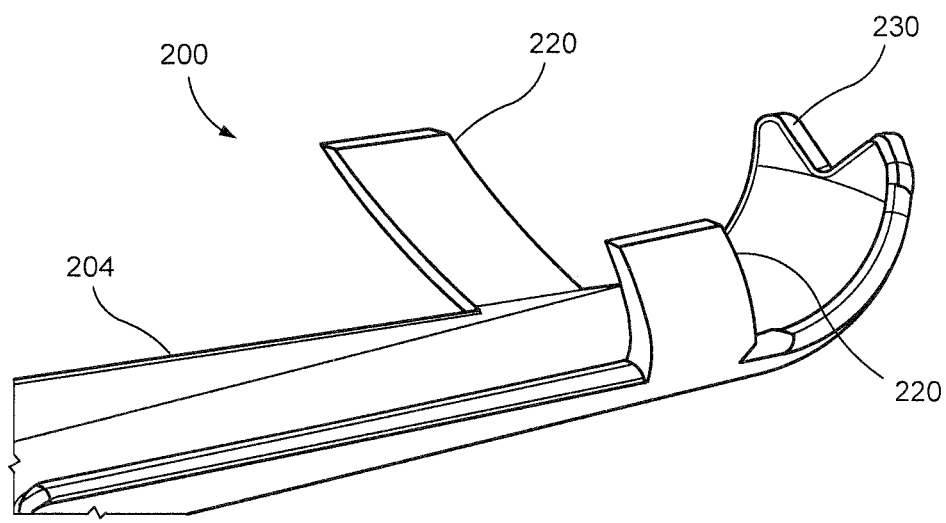
FIG. 8 shows a perspective view of a clip jaw according to another exemplary embodiment of the present disclosure.

As shown in FIG. 8, a device 200 according to another exemplary embodiment is substantially similar to the device 100, described above, comprising a pair of clip jaws 204, 206 slidable within a capsule 208 between an open configuration and a closed configuration. Rather than having a hook or barb 120 extending from the clip jaws 204, 206, however, the clip jaws 204, 206 have a wing teeth 220 design. Wing teeth 220 spread laterally outwards from clip jaws 204, 206 (i.e., away from a longitudinal axis of the device 200) and can be formed as C-shaped geometries that exist in clips today. Wing teeth 220 can be achieved by adding additional material to a current C-shape or created by cutting into a C-shape to create notches having sharper points to engage tissue. The wing teeth 220 are formed on portions of the jaws 204, 206 that do not enter the capsule even when the clip is drawn into the capsule to the maximum extent. Thus the wing teeth do not interfere with the operation of the device 200.

Figure 9:
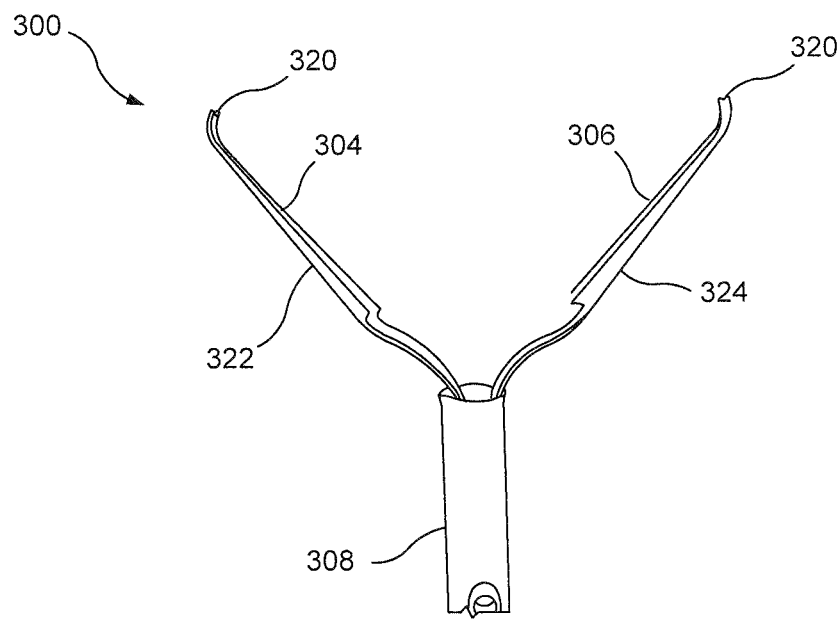
FIG. 9 shows a longitudinal top view of a device according to another exemplary embodiment of the present disclosure.

As shown in FIG. 9, a device 300 according to an alternate embodiment is substantially similar to the device 200, described above, comprising a pair of clip jaws 304, 306 slidable within a capsule 308 between an open configuration and a closed configuration. However, rather than having a wing teeth spreading laterally outwards from clip jaws in a C-shape geometry, the clip jaws 304, 306 have barbs 320 added to the distal end of clip wings 322, 324, allowing for better tissue retention when closing the clip jaws 304, 306. Barbs 320 become engaged when the physician moves the clip jaws 304, 306 to the open configuration and presses the clip jaws 304, 306 against the target tissue such that the clip jaws 304, 306 are parallel to the tissue surface. Barbs 320 are then able to capture tissue as the jaws 304, 306 are closed, causing the tissue to "tent" as the clip jaws 304, 306 are further retracted.

Figure 10:
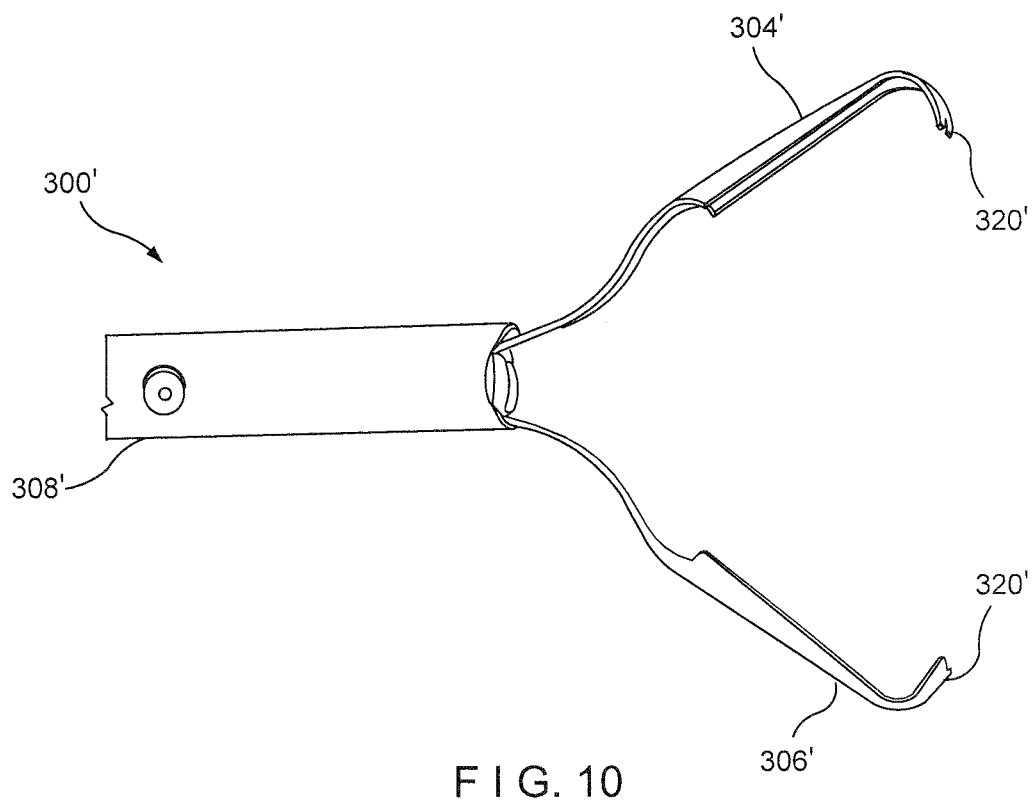
FIG. 10 shows a longitudinal top view of a device according to another exemplary embodiment of the present disclosure.
Figure 11:
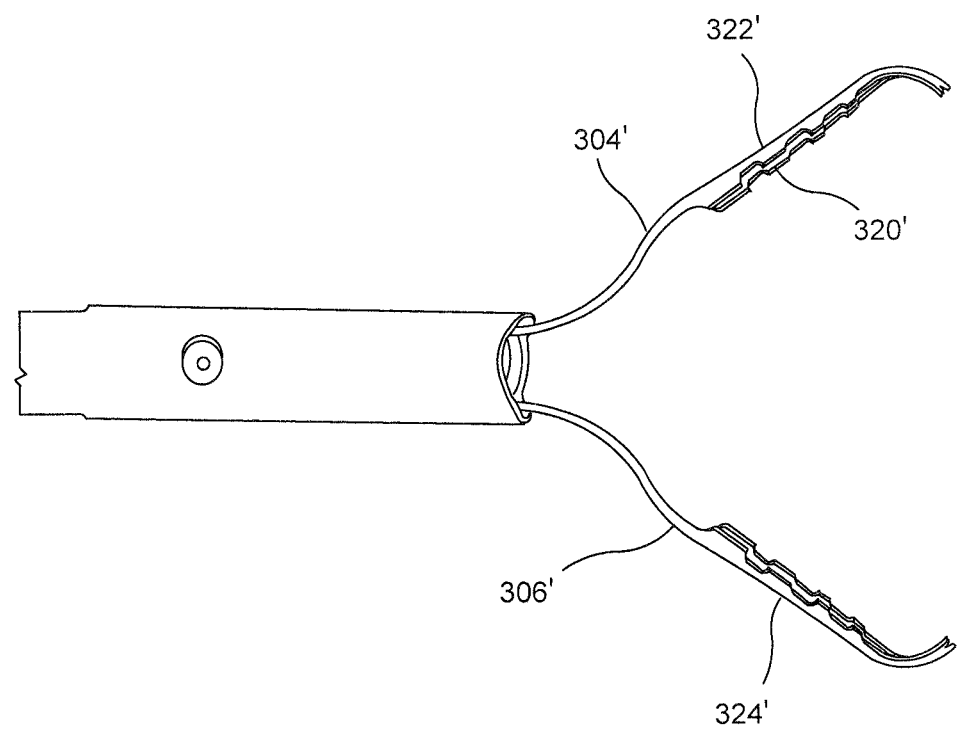
FIG. 11 shows a longitudinal top view of a device according to another exemplary embodiment of the present disclosure.

As shown in FIG. 10, a device 300' according to an alternate embodiment is substantially similar to the device 300. Clip jaws 304', 306' may have barbs 320' located at a distal end of clip wings 322, 324 as in device 300. However, in order to improve tissue retention of the distal portion 302' of the device 300', barb features 320' may be overbent such that they hook onto tissue as the clip jaws 304', 306' are retracted into the capsule 308'. In another embodiment shown in FIG. 11, in order to increase traction on the tissue as the clip is retracted into the capsule, one or more barb features 320' may be added to the sides of clip wings 322', 324' on clip jaws 304', 306' to ensure that tissue is caught upon retraction. Barb features 320' may also be placed on only one side of the distal portion 302' of device 300' to allow for a more controlled area of retention.

The devices 200, 300, 300' may be used in a manner substantially similar to the device 100. In particular, the clip jaws 204, 206, 304, 306, 304', 306' may be used to clip tissue as described above.

Variations may be made in the structure and methodology of the present disclosure, without departing from the spirit and the scope of the disclosure. Thus, it is intended that the present disclosure cover the modifications and variations of this disclosure that may be contemplated by a person of skill in the art.

What is claimed is:

1. A device for treating a tissue, comprising:
   a capsule extending longitudinally from a proximal end to a distal end and including a channel extending therethrough;
   clip jaws, proximal ends of which are slidably received within the channel of the capsule so that the clip jaws are movable between an open configuration, in which distal ends of the clip jaws extend distally past the distal end of the capsule to be separated from one another, and a closed configuration, in which the clip jaws are restrained via an interior surface of the capsule so that distal ends of the clips jaws are drawn toward one another, a distance between distal ends of the clip jaws in the open configuration being between 15 and 20 millimeters, the distal end of each of the clip jaws bending radially inward toward the other of the clip jaws; and
   a barb extending radially inward from a distal portion of each of the clip jaws, each of the barbs extending from an interior face of the distal portion of the corresponding clip jaws proximally of the bent distal end of the jaw at an angle between 20 and 90 degrees relative to the longitudinal axis of the clip jaws.

2. The device of claim 1, wherein the clip jaws are formed of a material having a yield strength between 200 and 260 ksi or a yield strain between 0.7 and 1.1 percent.

3. The device of claim 1, wherein the clip jaws are formed of 17-7 Stainless Steel.

4. The device of claim 1, wherein the distance between distal ends of the clip jaws in the open configuration is 16 millimeters.

5. The device of claim 1, wherein the distal portion of the clip jaws includes a stamped rib feature.

6. The device of claim 1, wherein the barb is formed as wing teeth.

7. The device of claim 1, wherein when the clip jaws are in the closed configuration, barbs on opposing clip jaws are configured to be staggered.

8. The device of claim 1, wherein when the clip jaws are in the closed configuration, barbs on opposing clip jaws are configured to touch.

9. The device of claim 1, wherein the clip jaws have a radius of curvature of 2.8 mm or less.

10. A clipping device, comprising:
    a proximal portion;
    a distal portion releasably coupled to the proximal portion so that the distal portion is deployable therefrom, the distal portion including:
    a capsule extending longitudinally from a proximal end to a distal end and including a channel extending therethrough;
    clip jaws extending from proximal ends slidably received within the channel of the capsule so that the clip jaws are movable between an open configuration, in which distal ends thereof extend distally past the distal end of the capsule to be separated from one another, and a closed configuration, in which the clip jaws are restrained via an interior surface of the capsule so that the distal ends thereof are drawn toward one another, a distance between distal ends of the clip jaws in the open configuration being between 15 and 18 millimeters, the distal end of each of the clip jaws bending radially inward toward the other of the clip jaws; and
    a barb extending radially inward from a distal portion of each of the clip jaws, each of the barbs extending from an interior face of the distal portion of the corresponding clip jaws proximally of the bent distal end thereof at an angle between 20 and 90 degrees relative to the longitudinal axis of the clip jaws; and
    a control member extending from a proximal end to a distal end, the distal end coupled to proximal ends of the clip jaws.

11. The device of claim 10, wherein the clip jaws are formed of a material having a yield strain between 0.7 and 1.1 percent or a yield strength between 200 and 260 ksi, including 17-7 Stainless Steel.

12. A method for treating target tissue, comprising:
    inserting a distal portion of a clipping device to a target area within a living body, the distal portion including a capsule and clip jaws slidably received within the capsule to be movable between an open configuration, in which distal ends of the clip jaws are separated from one another by a distance, at distal ends of the clip jaws, of between 15 and 20 millimeters, and a closed configuration, in which the distal ends of the clip jaws are drawn toward one another, each of the clip jaws including:
    a radially inward bend at a distal end thereof, the bent distal end of each jaw extending toward the other jaw; and
    a barb extending radially inward from an interior face of a distal portion of the clip jaws proximally of the bent distal end;
    positioning the clip jaws in contact with a target tissue; and
    clipping a target portion of tissue by positioning the target portion of tissue between the clip jaws in the open configuration and drawing the clip jaw toward the closed configuration to grip the target portion of tissue.

13. The method of claim 12, wherein positioning the clip jaws in contact with the target tissue includes gripping the target tissue with the at least one barb.

14. The method of claim 12, wherein the clip jaws are formed of a material having a yield strain between 0.7 and 1.1 percent or a yield strength between 200 and 260 ksi, including 17-7 Stainless Steel.

15. The method of claim 12, wherein each of the barbs extend from the corresponding clip jaw at an angle between 20 and 90 degrees relative from to the longitudinal axis of the clip jaws.

* * * * *